United States Patent [19]

Tanaka et al.

[11] Patent Number: 4,846,799
[45] Date of Patent: Jul. 11, 1989

[54] SET OF DOUBLE NEEDLES FOR INJECTING LIQUID MEDICINE

[75] Inventors: Masataka Tanaka, Togura; Masao Ohto, Togane; Tetsuo Sekine; Hiroshi Takahashi, both of Tokyo; Masaru Maruyama, Togura, all of Japan

[73] Assignee: Hakko Electric Machine Works Co., Ltd., Nagano, Japan

[21] Appl. No.: 2,993

[22] Filed: Jan. 13, 1987

[30] Foreign Application Priority Data

Oct. 9, 1986 [JP] Japan .............................. 61-155348[U]
Nov. 7, 1986 [JP] Japan .................................. 61-266384

[51] Int. Cl.$^4$ .............................................. A61M 5/00
[52] U.S. Cl. ...................................... 604/158; 604/164
[58] Field of Search ................. 604/158, 161, 164–166, 604/170, 264, 283, 281, 173, 191, 218, 257, 258; 128/912

[56] References Cited

U.S. PATENT DOCUMENTS

| 96,545 | 11/1869 | Brady | 285/330 |
|---|---|---|---|
| 2,219,605 | 10/1940 | Turkel | 604/164 |
| 3,312,220 | 4/1967 | Eisenberg | 604/164 |
| 3,487,834 | 1/1970 | Smith, Jr. | 604/165 |
| 3,782,381 | 1/1974 | Winnie | 604/164 |
| 4,013,080 | 3/1977 | Froning | 604/165 |
| 4,239,042 | 12/1980 | Asai | 604/164 |
| 4,511,356 | 4/1985 | Froning et al. | 604/164 |
| 4,613,329 | 10/1986 | Bodicky | 604/158 |
| 4,682,981 | 7/1987 | Suzuki et al. | 604/158 |

FOREIGN PATENT DOCUMENTS 1001034 12/1976 Canada .............................. 604/158

Primary Examiner—Stephen C. Pellegrino
Assistant Examiner—Ralph Lewis
Attorney, Agent, or Firm—Lowe, Price, LeBlanc, Becker & Shur

[57] ABSTRACT

A set of double needles of injecting liquid medicine comprises an inner needle and an outer needle into which the inner needle is inserted. The inner needle is longer than the outer needle and has a curved portion at the top thereof, so that the curved portion of the inner needle protrudes from the outer needle when the inner needle is fully inserted into the outer needle. On the other hand, the curved portion of the inner needle is straightened in the outer needle when the inner needle is retracted in the outer needle so that the inner needle can be rotated therein whereby the injecting point can be varied in a predetermined area in a single puncturing of the needles.

5 Claims, 3 Drawing Sheets

SET OF DOUBLE NEEDLES FOR INJECTING LIQUID MEDICINE

FIELD OF THE INVENTION

The invention relates to a set of double needles for injecting liquid medicine, and more particularly to a set of double needles for injecting liquid medicine by which an injecting point can be varied in a predetermined area in accordance with a single puncture of the skin.

BACKGROUND OF THE INVENTION

In FIGS. 1A to 1C, there is shown conventional double needles for injecting liquid medicine in which there is provided a set of double needles composed of an inner needle 1 and an outer needle 2 respectively having bevels 1a and 2a and being fixed to bases 3 and 4. FIG.1A shows the construction of a set of double needles in which the inner needle 1 is combined to be inserted into the outer needle 2, while FIGS. 1B and 1C show the inner and outer needles 1 and 2 which are separated from one another.

According to the conventional set of double needles for injecting liquid medicine, the double needles are punctured into a human body to reach the affected part thereof in the construction as shown in FIG. 1A whereafter liquid medicine is injected into the affected part through the inner needle 1 to the base 3 of which a syringe (not shown) containing the liquid medicine is connected. On the other hand, a large amount of liquid medicine is injected in a short period where a syringe (not shown) containing that amount of the liquid medicine is connected to the base 4 of the outer needle 4 from which the inner needle 1 is removed as shown in FIG. 1B.

In the conventional set of double needles for injecting liquid medicine, however, pain is increased for a patient because more than a single puncturing is needed where liquid medicine is injected into a plurality of the affected parts in a predetermined area and where the affected part to be injected is different.

SUMMARY OF THE INVENTION

Accordingly, it is an object of the invention to provide a set of double needles for injecting liquid medicine by which liquid medicine is injected into a plurality of the affected parts in a single puncturing thereof in a predetermined area thereby avoiding an increase in pain to a patient.

It is a further object of the invention to provide a set of double needles for injecting liquid medicine by which an injecting point can be varied in a predetermined area without increasing pain to a patient.

According to the invention, a set of double needles for injecting liquid medicine at each of two nearby locations through a common entry point of an injected body comprises an inner needle, and an outer needle into which said inner needle is slidably and rotatably inserted, each needle having a sharp delivery end and a receiving end communicating with a source of liquid medicine for pressurized injection thereof into said injected body at a selected first location in said body for injection through said sharp delivery end of said outer needle and a selected second location in said body through said sharp delivery end of said inner needle, said inner needle being longer than said outer needle and having a curved portion at the delivery end thereof which protrudes from the delivery end of said outer needle when fully inserted thereinto, said inner and outer needles cooperating such that said curved portion of said inner needle is straightened within said outer needle when retracted therein and said inner and outer needles are then rotatable to a different angular disposition relative to each other for subsequent reinsertion of said inner needle into said outer needle to thereby locate the sharp delivery end of said inner needle at a third location for injection of said liquid medicine thereat.

said curved portion being straightened within said outer needle when retracted in a predetermined length thereof.

BRIEF DESCRIPTION OF THE DRAWINGS

The invention will be described in detail in accordance with the following drawings wherein.

DESCRIPTION OF THE PREFERRED EMBODIMENT

Figure 1A:
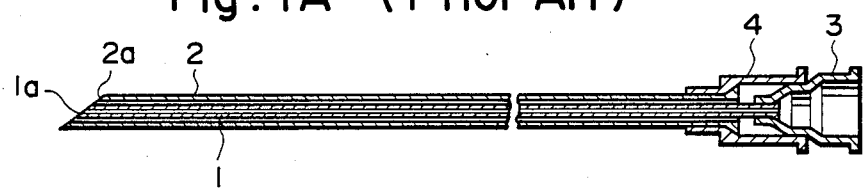
FIG. 1A is a cross-sectional view illustrating a conventional set for double needles of injecting liquid medicine.
Figure 1B:
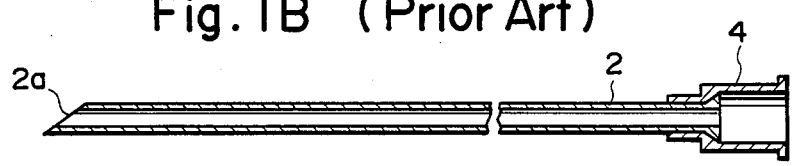
FIG. 1B is a cross-sectional view illustrating an outer needle in FIG. 1A.
Figure 1C:
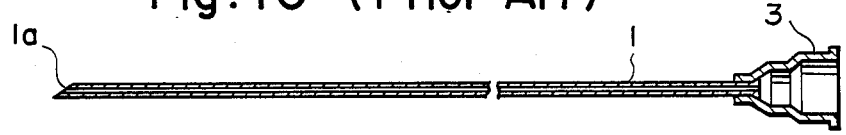
FIG. 1C is a cross-sectional view illustrating an inner needle in FIG. 1A.
Figure 2:
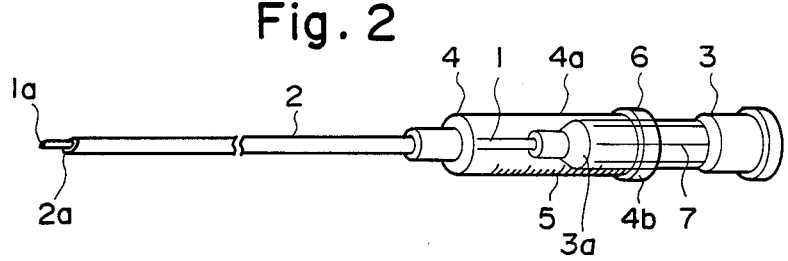
FIG. 2 is a perspective view illustrating a set of double needles for injecting liquid medicine in the first embodiment according to the invention.

In FIG. 2, there is shown a set of double needles for injecting liquid medicine in the first embodiment according to the invention in which there are provided an inner needle 1 having a curved portion at the end thereof and an outer needle 2 into which the inner needle is inserted. The inner and outer needles 1 and 2 are provided with bevels 1a and 2a respectively and the inner needle 1 is longer than the outer needle 2 so that the curved portion of the inner needle 1 protrudes from the outer needle 2 as described later in more detail when the inner needle 1 is fully inserted into the outer needle 2. Further, the inner and outer needles 1 and 2 are fixed to bases 3 and 4 respectively. The base 4 for the outer needle 2 is transparent and comprises a main body 4a having a measuring mark 5 distributed along its length and an end portion 4b having a standard mark 6 thereon. On the other hand, the base 3 for the inner needle 1 is provided with angle measurement mark 7 thereon.

Figure 3A:
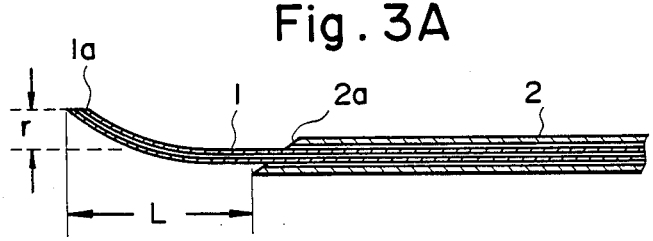
FIG. 3A to 3C are cross-sectional views each illustrating a relation between an inner and outer needles in the first embodiment according to the invention.

In operation, the bevel 1a for the inner needle 1 is positioned at the distance r from the center line because the inner needle 1 has the curved portion at the end thereof when the inner needle 1 protrudes from the bevel 2a for the outer needle 2 in a predetermined length L of, for instance, 25 mm as shown in FIG. 3A.

Figure 3B:
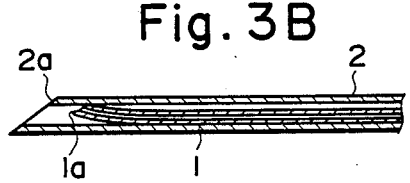

The inner needle 1 is straightened in the outer needle 2 in accordance with the resilient deformation thereof when the bevel 1a of the inner needle 1 is retracted into the outer needle 2 as shown in FIG. 3B. At this stage, the inner needle 1 is rotated by 180 degrees in accordance with the angle mark 7 on the base 3 and the standard mark 6 on the end portion 4b of the base 4.

Figure 3C:
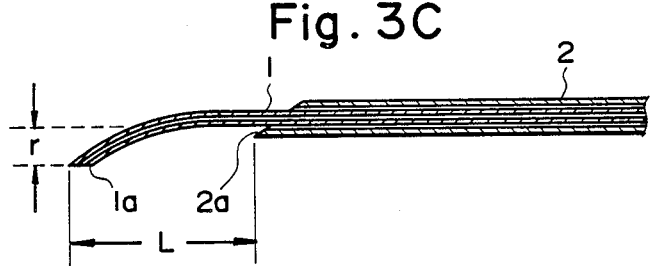

The bevel 1a is positioned at the distance r in the opposite direction from the center line due to the resilience thereof when the inner needle 1 protrudes from the bevel 2a for the outer needle 2 in a predetermined length L mentioned above as shown in FIG. 3C. The protruding length L is adjusted by determining the front end portion 3a for the base 3 in accordance with the measuring mark 5.

Figure 4:
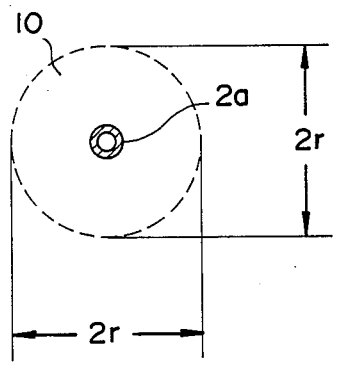
FIG. 4 is an explanatory view showing a covering area in a single puncturing of a set of double needles according to the invention.

It is understand from the explanation as shown in FIG. 4 that liquid medicine is projected to cover a predetermined area 10 having a diameter 2r the center of which is indicated at the bevel 2a for the outer needle 2.

Figure 5A:
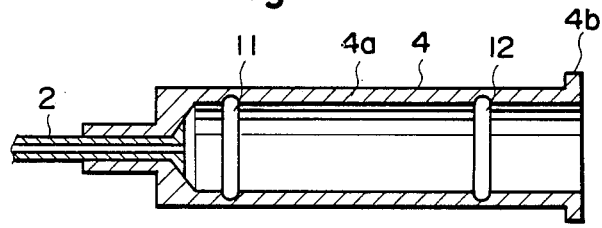
FIG. 5A is a cross-sectional view illustrating a base fixing an outer needle thereto in the second embodiment according to the invention.
Figure 5B:
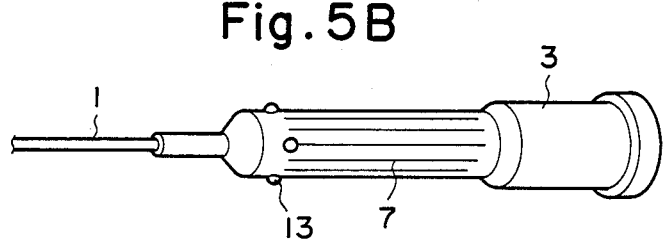
FIG. 5B is a perspective view illustrating a base fixing an inner needle thereto in the second embodiment according to the invention.

In FIGS. 5A and 5B, there is shown a set of double needles for injecting liquid medicine in the second embodiment according to the invention. The double needles are composed of an inner needle 1 which is fixed to a base 3 and an outer needle 2 which is fixed to a base 4. The base 3 is provided with projections 13 thereon each of which is deformed resiliently to be positioned at, for instance, 90 degrees interval while the base 4 is provided with grooves 11 and 12 on the inner surface thereof. In FIGS. 5A and 5B, like reference numerals indicate like parts as in FIG. 2.

In operation, the base 3 is positioned inside the base 4 such that the inner needle 1 is inserted into the outer needle 2. At this stage, the projections 13 are engaged into the groove 12 and the base 3 is rotated by a predetermined angle in accordance with the standard mark 6 on the end portion 4b and the angle mark 7 on the base 3. At the next stage, the base 3 is pushed forward so that the projections 13 are compressed whereby the base 3 is moved in a slidable manner inside the base 4 and that the projections 13 are engaged into the groove 11 whereby the base 3 is stopped while the inner needle 1 protrudes from the bevel 2a for the outer needle 2 in a predetermined length L as mentioned before. In the present embodiment, the force of engaging the projections 13 into the groove 11 is slightly greater than that of engaging the projections 13 into the groove 12 so that the handling of the double needles becomes easier.

Figure 6A:
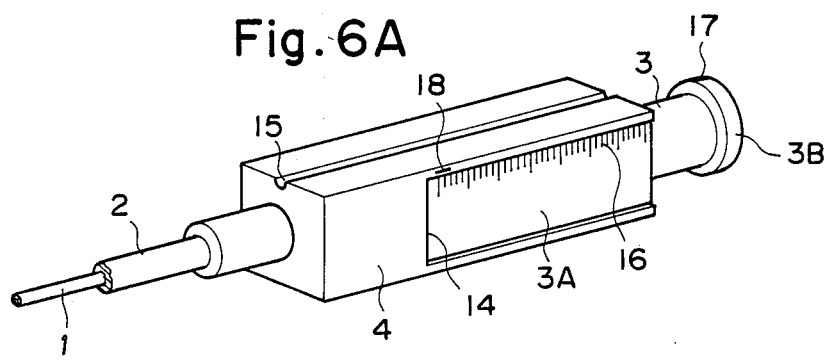
FIG. 6A is a perspective view illustrating a set of double needles for injecting liquid medicine in the third embodiment according to the invention.
Figure 6B:
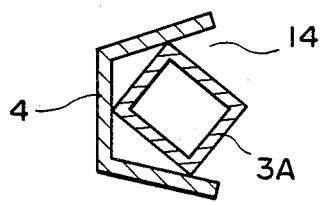
FIGS. 6B and 6C are cross-sectional views each illustrating a relation of bases for an inner and outer needles in the third embodiment according to the invention.
Figure 6C:
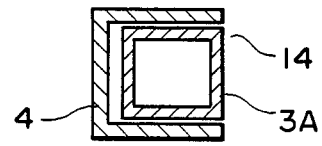

In FIGS. 6A to 6C, there is shown a set of double needles in the third embodiment according to the invention wherein a base 4 for an outer needle 2 is of a square having an opening portion 14 at the side thereof, a slit 15 to be utilized as a standard mark for the rotation at the other side thereof, and a mark 18 to be utilized as a standard point. On the other hand, the base 3 for the inner needle 1 comprises a square portion 3A and a circular portion 3B to which a syringe (not shown) is connected. A measuring mark 16 is provided on the square portion 3A and a standard mark 17 is provided on the circular portion 3B so that the corresponding relation between the inner and outer needles 1 and 2 is known in accordance with the relative positions of the marks 16 and 17 in regard to the slit 15 and mark 18.

In operation, the base 3 is pulled back such that the top edge thereof is positioned at the opening portion 14 whereby the base 3 is rotated as shown in FIG. 6B. In the rotation of the base 3, the base 4 is deformable so that the base 3 can be easily stopped after the rotation of 90, 180 or 270 degrees. Thereafter, the base 3 is pushed forward so that the inner needle 1 protrudes from the bevel 2a of the outer needle 2 in a predetermined length by checking the measuring mark 16 in regard to the mark 18.

Although the invention has been described with respect to specific embodiments for complete and clear disclosure, the appended claims are not to be thus limited but are to be construed as embodying all modification and alternative construction that may occur to one skilled in the art which fairly fall within the basic teaching herein set forth.

What is claimed is:

1. Apparatus for injecting liquid medicine at each of a plurality of user-selected nearby locations through a common entry point of the injected body, comprising:
    an inner needle, and an outer needle into which said inner needle is slidably and rotatably inserted, each of said needles having a sharp delivery end and a receiving end communicating with a respective source of liquid medicine for pressurized injection thereof into said injected body at a selected first location of said body for injection through said sharp delivery end of said outer needle and at a plurality of selected second locations in said body through said sharp delivery end of said inner needle;
    said inner needle being longer than said outer needle and having a curved portion at the delivery end thereof which protrudes from the delivery end of said outer needle when fully inserted thereinto, said inner and outer needles cooperating such that said curved portion of said inner needle is straightened within said outer needle when retracted therein and said inner and outer needles are then rotatable to different angular disposition relative to each other for subsequent reinsertion of said inner needle into said outer needle to thereby locate the sharp delivery end of said inner needle at a selected other one of said plurality of second locations for injection of said liquid medicine thereat.

2. The apparatus for injecting liquid medicine according to claim 1, wherein:
    said inner and outer needles are fixed to respective bases comprising individual fluid medicine reservoirs; and
    said base for said outer needle is transparent and has a standard reference mark for facilitating a predetermined amount of angular rotation of said inner needle base to said different disposition relative thereto and the body of said outer needle has measuring marks for facilitating determination of the length of said inner needle protruding from the delivery end of said outer needle.

3. The apparatus according to claim 2, wherein:
    said base for said inner needle has projections thereon; and
    said base for said outer needle is provided with grooves thereon into which said projections are engagable.

4. The apparatus according to claim 2, wherein:

the cross section of at least a portion of each of said bases for said inner and outer needles is square to allow the rotation and repositioning of the inner base relative to the outer base at 90 degree intervals.

5. The apparatus according to claim 3, wherein:
said base for said outer needle is provided with a first groove and a second groove, said grooves being formed such that a force for engaging said projections with the first groove is required to be larger than a force required to engage the projection with the second groove.

* * * * *